United States Patent [19]

Sasaki et al.

[11] Patent Number: 4,590,173

[45] Date of Patent: May 20, 1986

[54] PROCESS FOR PRODUCING ANTIMONY-CONTAINING OXIDE CATALYST SUPPORTED ON SILICA FOR USE IN FLUIDIZED BED REACTION

[75] Inventors: Yutaka Sasaki; Toshio Nakamura; Hiroshi Utsumi; Hiroshi Murata; Yoshimi Nakamura, all of Kanagawa, Japan

[73] Assignee: Nitto Chemical Industry Co., Ltd., Tokyo, Japan

[21] Appl. No.: 699,113

[22] Filed: Feb. 7, 1985

[30] Foreign Application Priority Data

Feb. 7, 1984 [JP] Japan ................................. 59-19369

[51] Int. Cl.$^4$ ..................... B01J 21/08; B01J 23/16; B01J 27/18
[52] U.S. Cl. .................................. 502/204; 502/210; 502/215; 502/214; 502/249
[58] Field of Search ............... 502/249, 204, 210, 215, 502/214

[56] References Cited

U.S. PATENT DOCUMENTS 3,397,153 8/1968 Sippel ............................. 502/249 X
3,686,138 8/1972 Yoshino et al. ...................... 502/249
4,410,450 10/1983 Sasaki et al. ..................... 502/215 X
4,447,558 5/1984 Sasaki et al. ..................... 502/210 X
4,536,483 8/1985 Sasaki et al. ..................... 502/215 X Primary Examiner—Carl F. Dees
Attorney, Agent, or Firm—Sughrue, Mion, Zinn, Macpeak and Seas

[57] ABSTRACT

A process for producing an antimony-containing oxide catalyst supported on silica for use in a fluidized bed reaction is described, by the steps of preparing a slurry containing an antimony compound, a polyvalent metal compound, and silica sol as the essential ingredients, heat treating the slurry at a pH of 7 or less and at a temperature of 40° C. or higher, and thereafter spray-drying the slurry and calcining the dried particles, wherein said silica sol has a multi-peak particle size distribution profile that is derived by using a mixture of silica sol A in an amount corresponding to form 10 to 90 wt % of the total silica in the catalyst and silica sol B in an amount corresponding to 90 to 10 wt % of the total silica in the catalyst, with silica sols A and B having different average particle sizes, provided that the relations $3 < da < 100$ and $0.1 < da/db < 0.9$ are satisfied by da (m$\mu$), the average particle size of silica sol A, and db (m$\mu$), the average particle size of silica sol B.

8 Claims, No Drawings

PROCESS FOR PRODUCING ANTIMONY-CONTAINING OXIDE CATALYST SUPPORTED ON SILICA FOR USE IN FLUIDIZED BED REACTION

BACKGROUND OF THE INVENTION

The present inventon relates to an improved process for producing an antimony-containing oxide catalyst supported on silica for use in a fluidized bed reaction. More particularly, the invention relates to a process for producing a catalyst for use in the oxidation, ammoxidation or oxidative dehydrogenation of organic compounds.

Many catalysts are known for use in the oxidation, ammoxidation, or oxidative dehydrogenation of organic compounds. Particularly good results are obtained by antimony-containing catalysts such as the antimony-tin oxide composition described in U.S. Pat. No. 3,152,170, the oxide composition containing antimony and iron, cobalt and/or nickel oxides described in Japanese Patent Publication No. 19111/63, and the antimony-uranium oxide composition described in U.S. Pat. No. 3,303,151.

In most cases, these catalysts are used as is supported on carriers such as silica, alumina, and titania for the primary purpose of imparting strength to the catalyst. Prior art techniques for attaining this purpose are described in U.S. Pat. Nos. 3,341,471, 3,657,155, and 3,686,138. While the techniques described in these prior art references relate to the production of antimony-containing oxide catalysts, they are not completely satisfactory for the purpose of producing catalysts having high activity and good physical properties. One problem common to the catalysts produced by these methods is low strength, which is particularly significant with respect to catalysts for use in fluidized bed reactions.

Sufficient catalyst strength is important for reactions in fluidized beds. Catalysts having high activity are not suitable for industrial use in their strength is low; in such a case, the catalyst loss is undesirably large (due to scattering to the outside of the system) and it becomes difficult to operate the system in a steady manner. Even if this worst case does not occur, the consumption of the catalyst is increased so as to undesirably increase the manufacturing cost of the end product.

Japanese Patent Application (OPI) No. 11045/83 (The term "OPI" as used herein refers to a "published unexamined Japanese patent application".) (corresponding U.S. Pat. No. 4,377,500) proposes using a mixture of fumed silica and silica sol as a carrier for supporting antimonate-based catalyst. It claims that by using this carrier material, an antimonate-based catalyst having good catalytic characteristics and high attrition resistance can be prepared. However, fumed silica is a powder which is to bulky that great inconvenience is involved in its handling. If fumed silica is mixed with silica sol, the resulting catalyst has low bulk density and low particle density as well as poor mechanical strength. Thus, it is seen that the method of Japanese Patent Application (OPI) No. 11045/83 (corresponding to U.S. Pat. No. 4,377,500) involves a complicated procedure in catalyst preparation, and the resulting catalyst has a relatively small strength that will cause increased catalyst loss during service.

A proposal for using a mixture of silica sols having different particle sizes with a view to producing a silica gel of low bulk density is shown in U.S. Pat. No. 3,397,153. The specification of this patent contains an Example which relates to the production of a catalyst supported on silica which is to be used in a fixed bed reaction and which contains phosphorus, molybdenum, and bismuth.

A catalyst for use in a fluidized bed reaction suffers from an increased catalyst loss if it has an excessively low bulk density and this is because the low bulk density leads to a catalyst of small strength which easily scatters to the outside of the reaction system. If, on the other hand, the catalyst has an excessively high bulk density, poor fluidization occurs in the bed. It is therefore desired that catalysts for use in fluidized bed reactions have a proper bulk density relative to the specific object and at the same time have sufficient mechanical strength.

U.S. Pat. No. 3,397,153 makes no mention of catalyst strength. Nor does it suggest the production of an antimony-containing oxide catalyst of the type contemplated by the present invention, i.e., a catalyst with improved strength for use in fluidized bed reactions.

Thus, the proposals made in U.S. Pat. Nos. 4,377,500 and 3,397,153 are not improvements of the methods described in U.S. Pat. Nos. 3,657,155 and 3,686,138, nor do they suggest the method of the present invention.

SUMMARY OF THE INVENTION

The present invention overcomes the defects of the prior art techniques mentioned above, and provides a process for producing a highly active and strong antimony-containing oxide catalyst supported on silica. The method of the present invention is particularly effective in producing a fluidized bed catalyst.

More specifically, the present invention provides a process for producing an antimony-containing oxide catalyst supported on silica for use in a fluidized bed reaction by the steps of preparing a slurry containing an antimony compound, a polyvalent metal compound and a silica sol as the essential ingredients, heat-treating the slurry at a pH of 7 or less and at a temperature of 40° C. or higher, and thereafter drying the slurry and calcining the dried particles, wherein the improvement comprises that said silica sol has a multi-peak particle size distribution profile that is derived by using a mixture of silica sol A in an amount corresponding to 10 to 90 wt% of the total silica in the catalyst and silica sol B in an amount corresponding to 90 to 10 wt% of the total silica in the catalyst, with silica sols A and B having different average particle sizes, provided that the relations "$3 < da < 100$" and "$0.1 < da/db < 0.9$" are satisfied by da (m$\mu$), the average particle size of silica sol A, and db (m$\mu$), the average particle size of silica sol B.

Of course, according to the present invention, silica gel A and/or silica sol B may be a mixture of two or more silica sols.

The antimony-containing oxide catalyst for use in fluidized beds reaction that if produced by the process of the present invention has an improved strength and an activity at least equal as compared to the strength and activity of the catalyst produced by using a silica sol having a single-peak particle size distribution profile.

The method of the present invention is particularly effective in producing an antimony-containing oxide catalyst supported on silica, especially fluidized bed catalyst.

A preferred catalyst according to this invention has a composition represented by the empirical formula $$Me_aSb_bX_cQ_dR_eO_f(SiO_2)_g$$

wherein

Me represents at least one element selected from the group consisting of Fe, Co, Ni, Sn, U, Cr, Cu, Mn, Ti, Th, and Ce;

X represents at least one element selected from the group consisting of V, Mo, and W;

Q represents at least one element selected from the group consisting of Li, Na, K, Rb, Cs, Be, Mg, Ca, Sr, Ba, Y, La, Th, Zr, Hf, Nb, Ta, Re, Ru, Os, Rh, Ir, Pd, Pt, Ag, Zn, Cd, Al, Ga, In, Tl, Ge, Pb, As, and Se, and preferably at least one element selected from the group consisting of Mg, Ca, Zr, Nb, Ta, Zn, Al, Ga, and Pb;

R represents at least one element selected from the group consisting of B, P, Te, and Bi; and the subscripts a, b, c, d, e, and g represent atomic ratios and are respectively within the ranges a is from 5 to 15;
b is from 5 to 100 (preferably from 10 to 60);
c is from 0 to 15 (preferably from 0.1 to 10);
d is from 0 to 20 (preferably from 0.1 to 10);
e is from 0 to 10 (preferably from 0.05 to 5);
g is from 10 to 200 (preferably from 20 to 100); and
f refers to a number of oxygen atoms corresponding to the oxide as formed by bonding the respective constituent elements.

The catalyst prepared in the present invention consists of generally spherical particles having an average diameter in the range of from 5 to 200 μm.

Illustrative antimony compounds that may be used in the present invention include metallic antimony as oxidized with nitric acid, antimony nitrate, basic antimony nitrate, antimony trioxide, antimony tetroxide, antimony pentoxide, antimonic acid, polyantimonic acid, antimony trichloride, antimony pentachloride, antimony trichloride as oxidized with nitric acid, antimony trioxide as oxidized with hydrogen peroxide, and antimony pentoxide sol.

The polyvalent metal compound used in the present invention is a compound of an element having divalence or higher valencies and it is a compound of at least one element selected from among the constituent elements of the catalyst. This compound may be an oxide, a hydroxide, or a nitrate of the element defined above.

The material used for any other catalyst component may be selected from among the oxide, hydroxide, and nitrate of the respective constituent elements.

Silica sol is conveniently selected from among the commercially available products. It may be synthesized by any of the known methods such as ion exchange, gel peptization, dialysis and ultrafiltration. The synthesis of silica sol includes the step of producing highly polymerized molecules of silicic acid by condensation polymerization, and the conditions for the production of these molecules determine the size of silica colloid particles. Generally speaking, given the same conditions for producing such molecules, silica colloid particles of the same size are obtained, providing a substantially uniform size distribution.

The silica sols used in the present invention have average particle sizes in the range of 1 to 1,000 mμ. For the purpose of producing a stable silica sol, the particle size generally in the range of from 3 to 100 mμ, and preferably from 5 to 50 mμ, may be employed.

The particle size of the silica sol may be determined by any known technique, such as surface area measurement, microscopic observation, or titration with sodium hydroxide.

The process of the present invention proceeds as follows: an aqueous slurry containing an antimony compound, a polyvalent metal compound, at least two silica sols having different particle sizes, and materials for other optionally provided catalyst components, as well as ammonium ions and nitrate ions, is prepared; after adjusting the pH to 7 or less, and preferably 4 or less, the slurry is heated at a temperature between about 40° C. and about 150° C., and preferably between about 80° C. and about 120° C., for a period of at least 20 minutes, and preferably between 30 minutes and 10 hours, while maintaining the slurry state; the slurry is then dried, followed by spray drying to obtain fine spherical particles, which are then calcined (preferably after calcination at 200° to 600° C.) at a temperature between about 400 and about 1,100° C., and preferably between 500° and 950° C., thereby obtaining the end catalyst.

The slurry obtained after the pH adjustment, but before the heat treatment, must contain the antimony compound, polyvalent metal compound, and silica sols simultaneously. Part of each component may be added after the heat treatment, but a catalyst having appropriate properties cannot be obtained if the whole part of any one of the three components is added after the heat treatment.

While various modifications may be made to the process of the present invention, the important thing is that at least two silica sols having different particle sizes are used. If the two silica sols are respectively designated as A and B, silica sol A is used in an amount corresponding to from 10 to 90 wt% (weight percent), preferably 20 to 80 wt%, of the total silica in the catalyst, and silica sol B is used in an amount corresponding to 90 to 10 wt%, preferably 80 to 20 wt%, of the total silica in the catalyst.

The silica sols A and B need not be preliminarily mixed. The only requirement is that both be present in the slurry before it is adjusted to a pH of 7 or less. Therefore, silica sols A and B may be separately and independently mixed with one or both of the antimony compound and the polyvalent metal compound. For example, part or all of the silica sol A may be mixed with the antimony compound and polyvalent metal compound and to the resulting slurry is added silica sol B (and the remainder of silica sol A if only part of it has been used). Other variations may also be employed for mixing silica sols A and B. Provided that the two silica sols are present in the slurry before pH adjustment, the order of addition of silica sols A and B, antimony compound, and polyvalent metal compound is not critical.

If the average particle sizes of silica sols A and B are written as da (mμ) and db (mμ), respectively, the following relations are preferably satisfied:

$$3 < da < 100$$

$$0.1 < da/db < 0.9$$

With respect to the foregoing, it is again nated that silica sol A and/or silica sol B may be a mixture of two or more silica sols.

The antimony-containing oxide catalyst supported on silica thus prepared for use in fluidized bed reactions has good physical properties and activity.

The advantages of the present invention are hereunder described in greater detail by reference to the following working examples and compartive examples, wherein the silica sols specified below were used.

| Silica Sol | SiO2 Content (wt %) | Particle Size (mμ) | pH | Viscosity (cps) |
| --- | --- | --- | --- | --- |
| I | 20.1 | 8 | 8.5 | 1.9 |
| II | 20.0 | 13 | 3.2 | 2.8 |
| III | 20.5 | 16 | 8.2 | 4.3 |
| IV | 20.0 | 45 | 3.2 | 2.5 |

Two tests were conducted to check the strength of the fluidized bed catalyst samples prepared in the examples.

(1) Attrition Resistance Test

The method described in "Test Methods for Synthetic Cracking Catalysts" (American Cyanamid Co., Ltd., 6/31-4m-1/57), which is known as a collection of testing methods for catalysts used in fluid catalytic cracking, was used. The attrition loss (%) was determined by the following formula:

$$\text{Attrition loss (\%) } R = \frac{B}{C - A} \times 100$$

wherein
A = the weight (g) of the catalyst portion that wore away in the period of 0 to 5 hrs;
B = the weight (g) of the catalyst portion that wore away in the period of 5 to 20 hrs;
C = the weight (g) of the catalyst tested.

For the purpose of the experimental testing, C was selected at 50. The higher the attrition resistance, the smaller the R value (%) the catalyst showed.

(2) Crushing Strength Test

A catalyst was screened through a micromesh sieve to obtain a test sample having particle sizes between 35 and 40 μm. A portion (0.025 g) of this sample was put into a 4 cc polystyrene cylindrical vessel together with steel balls (2 mmϕ). The sample was pulverized by a 90 sec treatment in a mixer mill (manufactured by SPEX Industries, Inc.). A particle size distribution profile was measured for the crushed sample and the K value (%) representing the proportion of the amount of particles with a size of 16 μm or less relative to the amount of the sample initially charged was determined. The larger the strength of the catalyst, the smaller is the K value shown.

The activity of each catalyst sample was determined by performing ammoxidation of propylene in the following manner.

A fluidized bed reactor having a fluidized bed zone with an inside diameter of 2.5 cm and a height of 40 cm was charged with the catalyst and fed with a gas of the following composition in order to perform ammoxidation at atmospheric pressure:

O2 (as air)/propylene = 2.2 (mol/mol)

NH3/propylene = 1.1 (mol/mol)

EXAMPLE 1

A catalyst having the empirical formula $W_{0.2}Mo_{0.5}Te_{1.4}Cu_4Fe_{11}Sb_{25}O_{75.4}(SiO_2)_{60}$ was prepared by the following procedure.

Electrolytic iron powder (68.4 g) was provided. Nitric acid (530 ml, specific gravity: 1.38) was mixed with pure water (660 ml) and the mixture was heated. To the heated mixture, the electrolytic iron powder was added in small portions. It was confirmed that a complete solution had formed.

Copper nitrate (107.5 g) was dissolved in the solution of iron nitrate. To the resulting solution of iron-copper nitrate, 998 g of silica sol I and 1,003 g of silica sol II were sequentially added. Antimony trioxide (405 g) was added to the resulting silica sol solution. To the solution, 15% ammonia water was added in small amounts until the solution had a pH of 2. The slurry obtained was heated at 95° C. for 4 hours.

Ammonium paratungstate (5.8 g), ammonium paramolybdate (9.8 g) and telluric acid (35.8 g) were dissolved in pure water (500 ml). The resulting solution was added to the previously prepared slurry and the mixture was agitated thoroughly before spray drying. Spherical particles were obtained by spray drying, and then they were calcined in three stages, first at 200° C. for 4 hours, then at 450° C. for 4 hours and finally at 780° C. for 4 hours.

EXAMPLE 2

A catalyst was prepared as in Example 1 except that silica sols I and II were replaced by silica sols II and III, which were used in respective amounts of 1,003 g and 979 g.

EXAMPLE 3

A catalyst was prepared as in Example 1 except that in place of silica sols I and II, silica sols II and III were used in amounts of 1,505 g and 489 g, respectively.

EXAMPLE 4

A catalyst was prepared as in Example 1 except that silica sols I and II were replaced by silica sols I and III, which were used in amounts of 998 g and 979 g, respectively.

EXAMPLE 5

A catalyst was prepared as in Example 1 except that silica sols I and II were replaced by silica sols I and IV, which were used in respective amounts of 1,497 g and 502 g.

EXAMPLE 6

A catalyst having the empirical formula $Mo_{0.5}Te_{1.5}Cu_{4.5}Fe_{11}Sb_{25}O_{75.5}(SiO_2)_{50}$ was prepared by the following procedure.

Electrolytic iron powder (73.2 g) was provided. Nitric acid (590 ml, specific gravity: 1.38) was mixed with pure water (740 ml) and the mixture was heated. To the mixture, the electrolytic iron powder was added in small portions. It was confirmed that a complete solution had formed. Metallic tellurium powder (22.8 g) was then dissolved in the solution.

Copper nitrate (129 g) was dissolved in the solution of iron nitrate. To the resulting solution of iron-tellurium-copper nitrate, 445 g of silica sol I and 1,342 g of silica sol II were sequentially added. Antimony trioxide (434 g) was added to the resulting silica sol solution. To the resulting slurry, a solution of ammonium paramolybdate (10.5 g) in pure water (100 ml) was added. To the mixture, 15% ammonia water was added in small amounts until the solution had a pH of 2. The slurry obtained was heated at 100° C. for 3.5 hours. The heated slurry was spray dried after thorough agitation. Spherical particles were obtained by the spray drying, and then they were calcined in three stages, calcined at 200° C. for 4 hours, then at 400° C. for 4 hours, and finally at 790° C. for 3 hours.

EXAMPLE 7

A catalyst having the empirical formula $Fe_{10}Co_{1.5}Ni_{1.5}Sb_{25}W_{0.5}Te_{1.2}B_{0.5}O_{72.7}(SiO_2)_{50}$ was prepared as in Example 1, except that Co and Ni were added as nitrate salts, boric acid anhydride was added as a B source, silica sols I and III were used as silica sources, and the final calcination of the spherical particles was conducted at 815° C. for 3 hours.

EXAMPLE 8

A catalyst having the empirical formula $Fe_{10}Sn_{0.5}U_1Sb_{25}W_{0.3}Mo_{0.3}Zr_{0.2}Ga_{0.2}Te_{1.0}Bi_{0.5}O_{74.2}(SiO_2)_{30}$ was prepared as in Example 1, except that the Sn source was metallic tin as oxidized with nitric acid and the U, W, Zr, Ga, Te and Bi sources were respectively uranyl nitrate, ammonium paratungstate, zirconium oxynitrate, gallium nitrate, telluric acid, and bismuth nitrate. Silica sols I and III were used as silica sources, and the final calcination was conducted at 790° C. for 4 hours.

EXAMPLE 9

A catalyst having the empirical formula $Fe_{10}Cr_1Sb_{20}W_{0.5}Nb_{0.2}Ta_{0.2}P_{0.5}O_{59.5}(SiO_2)_{60}$ was prepared as in Example 1, except that the Cr, Nb, Ta and P sources were chromium nitrate, niobium oxalate, tantalum pentoxide and phosphoric acid, respectively. Silica sols II and III were used as silica sources, and the final calcination was conducted at 850° C. for 3 hours.

EXAMPLE 10

A catalyst having the empirical formula $Fe_{10}Mn_2Sb_{3.0}Mo_{0.5}Zn_{0.5}Bi_{0.5}P_{0.5}O_{83}(SiO_2)_{70}$ was prepared as in Example 1, except that Mn, Zn and Bi were used as nitrate salts whereas the P source was phosphoric acid. Silica sols II and III were used as silica sources and the final calcination was conducted at 820° C. for 5 hours.

EXAMPLE 11

A catalyst having the empirical formula $Fe_8Ti_2Sb_{20}V_{0.3}Al_1Te_{1.1}O_{60.5}(SiO_2)_{55}$ was prepared as in Example 1, except that the Ti, V and Te sources were titanium dioxide, ammonium metavanadate and tellurium dioxide whereas Al was used as a nitrate salt. Silica sols II and III were used as silica sources and the final calcination was conducted at 800° C. for 4 hours.

EXAMPLE 12

A catalyst having the empirical formula $Fe_{10}Cu_3Ni_{0.5}Sb_{35}W_{0.5}Mo_{0.2}Pb_{0.5}Te_{1.5}O_{155.1}(SiO_2)_{60}$ was prepared as in Example 1, except that Ni and Pb were used as nitrate salts and the Te source was telluric acid. Silica sols II and III were used as silica sources, and the final calcination was conducted at 770° C. for 3 hours.

COMPARATIVE EXAMPLE 1

A catalyst was prepared as in Example 1 except that only silica sol I was used as a silica source in an amount of 1,996 g.

COMPARATIVE EXAMPLE 2

A catalyst was prepared as in Example 1 except that only silica sol III was used as a silica source in an amount of 1,957 g.

COMPARATIVE EXAMPLE 3

A catalyst was prepared as in Example 6 except that only silica sol II was used as a silica source in an amount of 1,789 g.

COMPARATIVE EXAMPLE 4

A catalyst having the empirical formula $Fe_{10}Co_{1.5}Ni_{1.5}Sb_{25}W_{0.5}Te_{1.2}B_{0.5}O_{72.7}(SiO_2)_{50}$ was prepared as in Example 5 except that only silica sol III was used as a silica source.

COMPARATIVE EXAMPLE 5

A catalyst having the empirical formula $Fe_{10}Sn_{0.5}U_1Sb_{25}W_{0.3}Mo_{0.3}Zr_{0.2}Ga_{0.2}Te_{1.0}Bi_{0.5}O_{74.2}(SiO_2)_{30}$ was prepared as in Example 6 except that only silica sol III was used as a silicon source.

COMPARATIVE EXAMPLE 6

A catalyst having the empirical formula $Fe_{10}Cr_1Sb_{20}W_{0.5}Nb_{0.2}Ta_{0.2}P_{0.5}O_{59.5}(SiO_2)_{60}$ was prepared as in Example 7 except that only silica sol III was used as a silica source.

COMPARATIVE EXAMPLE 7

A catalyst having the empirical formula $Fe_{10}Mn_2Sb_{3.0}Mo_{0.5}Zn_{0.5}Bi_{0.5}P_{0.5}O_{83}(SiO_2)_{70}$ was prepared as in Example 8 except that only silica sol III was used as a silica source.

COMPARATIVE EXAMPLE 8

A catalyst having the empirical formula $Fe_8Ti_2Sb_{20}V_{0.3}Al_1Te_{1.1}O_{60.5}(SiO_2)_{55}$ was prepared as in Example 9 except that only silica sol III was used as a silica source.

COMPARATIVE EXAMPLE 9

A catalyst having the empirical formula $Fe_{10}Cu_3Ni_{0.5}Sb_{35}W_{0.5}Mo_{0.2}Pb_{0.5}Te_{1.5}O_{155.1}(SiO_2)_{60}$ was prepared as in Example 10 except that only silica sol III was used as a silica source.

The physical properties of the catalysts prepared in the Examples and Comparative Examples are shown in Table 1, and the results of activity tests conducted with these catalysts are listed in Table 2.

TABLE 1

| Example No. | Silica Sol Mixing Ratio A (wt %) | | B (wt %) | Particle Size Ratio da/db | Final Calcination Temperature (°C. × 3 hr) | Physical Properties | | |
|---|---|---|---|---|---|---|---|---|
| | | | | | | Apparent Bulk Density (g/ml) | Strength Attrition Resistance R Value | Crushing Strength K Value |
| Example 1 | I | 50 | II 50 | 0.62 | 780 | 1.23 | 0.5 | 22.0 |
| Example 2 | II | 50 | III 50 | 0.81 | 780 | 1.15 | 0.7 | 23.2 |
| Example 3 | II | 75 | III 25 | 0.81 | 780 | 1.18 | 0.5 | 26.5 |
| Example 4 | I | 50 | III 50 | 0.50 | 780 | 1.16 | 0.6 | 23.1 |
| Example 5 | I | 75 | IV 25 | 0.18 | 780 | 1.25 | 0.4 | 28.1 |

TABLE 1-continued

| Example No. | Silica Sol | | | | Final Calcination Temperature (°C. × 3 hr) | Apparent Bulk Density (g/ml) | Attrition Resistance R Value | Crushing Strength K Value |
|---|---|---|---|---|---|---|---|---|
| Example 6 | I | 25 | II | 75 | 0.62 | 790 | 1.22 | 0.4 | 20.1 |
| Example 7 | I | 50 | III | 50 | 0.62 | 815 | 0.88 | 1.3 | 23.1 |
| Example 8 | I | 50 | III | 50 | 0.62 | 790 | 0.91 | 2.0 | 30.5 |
| Example 9 | II | 50 | III | 50 | 0.81 | 850 | 1.04 | 0.8 | 20.0 |
| Example 10 | II | 50 | III | 50 | 0.81 | 820 | 0.90 | 1.9 | 34.1 |
| Example 11 | II | 50 | III | 50 | 0.81 | 800 | 0.97 | 2.0 | 27.5 |
| Example 12 | II | 50 | III | 50 | 0.81 | 770 | 0.89 | 2.4 | 38.8 |

| Example No. | Silica Sol | Final Calcination Temperature (°C. × 3 hr) | Apparent Bulk Density (g/ml) | Attrition Resistance R Value | Crushing Strength K Value |
|---|---|---|---|---|---|
| Comparative Example 1 | I alone | 780 | 1.18 | 0.7 | 36.1 |
| Comparative Example 2 | III alone | 780 | 1.14 | 0.9 | 39.3 |
| Comparative Example 3 | II alone | 790 | 1.20 | 0.6 | 38.5 |
| Comparative Example 4 | III alone | 815 | 0.85 | 1.5 | 38.2 |
| Comparative Example 5 | III alone | 790 | 0.87 | 2.1 | 40.5 |
| Comparative Example 6 | III alone | 850 | 1.01 | 1.1 | 22.0 |
| Comparative Example 7 | III alone | 820 | 0.82 | 2.2 | 49.6 |
| Comparative Example 8 | III alone | 800 | 0.95 | 2.3 | 30.8 |
| Comparative Example 9 | III alone | 770 | 0.83 | 3.3 | 51.7 |

TABLE 2

| Example No. | Reaction Temperature (°C.) | Contact Time (sec) | Acrylonitrile Yield (%) | Total Propylene Conversion (%) |
|---|---|---|---|---|
| Example 2 | 435 | 4.0 | 83.2 | 98.5 |
| Example 3 | 435 | 4.0 | 83.0 | 98.9 |
| Example 7 | 425 | 4.0 | 80.2 | 98.2 |
| Example 8 | 425 | 4.0 | 79.0 | 98.5 |
| Example 9 | 430 | 4.5 | 73.1 | 96.7 |
| Example 10 | 425 | 4.5 | 74.1 | 97.0 |
| Example 11 | 430 | 4.0 | 78.4 | 99.2 |
| Example 12 | 430 | 3.5 | 82.1 | 99.5 |
| Comparative Example 2 | 435 | 4.0 | 83.0 | 98.3 |
| Comparative Example 4 | 425 | 4.0 | 80.0 | 97.9 |
| Comparative Example 5 | 425 | 4.0 | 78.8 | 97.3 |
| Comparative Example 6 | 430 | 4.5 | 70.9 | 95.0 |
| Comparative Example 7 | 425 | 4.5 | 73.1 | 95.5 |
| Comparative Example 8 | 430 | 4.0 | 77.9 | 98.4 |
| Comparative Example 9 | 430 | 3.5 | 80.9 | 98.7 |

While the invention has been described in detail and with reference to specific embodiments thereof, it will be apparent to one skilled in the art that various changes and modifications can be made therein without departing from the spirit and scope thereof.

What is claimed is:

1. In a process for producing an antimony-containing oxide catalyst supported on silica for use in a fluidized bed reaction by the steps of preparing a slurry containing an antimony compound, a polyvalent metal compound, and a silica sol as the essential ingredients, heat treating the slurry at a pH of 7 or less and at a temperature of 40° C. or higher, and thereafter drying the slurry and calcining the dried particles, the improvement wherein said silica sol has a multi-peak particle size distribution profile that is derived by using a mixture of silica sol A in an amount corresponding to from 10 to 90 wt% of the total silica in the catalyst and silica sol B in an amount corresponding to 90 to 10 wt% of the total silica in the catalyst, with silica sols A and B having different average particle sizes, provided that the relations $3 < da < 100$ and $0.1 < da/db < 0.9$ are satisfied wherein da (mμ) is the average particle size of silica sol A, and db (mμ) is the average particle size of silica sol B.

2. A process according to claim 1, wherein a mixture of silica sols A and B is first prepared and then a slurry is prepared from the antimony compound, polyvalent metal compound, and said silica sol mixture.

3. A process according to claim 1, wherein silica sols A and B are mixed separately and independently with one or both of the antimony compound and the polyvalent metal compound during the step of slurry preparation before pH adjustment.

4. A process according to claim 3, wherein part or all of silica sol A or B is mixed with one or both of the antimony compound and the polyvalent metal compound, and subsequently, the remaining silica sol of A and B is added to the mixture to prepare a slurry.

5. A process according to claim 3, wherein part of silica sols A and B is mixed with one or both of the antimony compound and the polyvalent metal compound, and subsequently, the remaining silica sols of A and B are added to the mixture to prepare a slurry.

6. A process according to claim 1, wherein the drying of the slurry is performed by spray drying so as to form fine spherical particles, which are subsequently calcined at from 200° to 600° C., and finally calcined at from 500° to 950° C.

7. A process according to claim 1, wherein the polyvalent metal compound is a compound of at least one element selected from the group consisting of iron, cobalt, nickel, tin, uranium, chromium, copper, maganese, titanium, vanadium, molybdenum, tungsten, tellurium, bismuth, arsenic, thorium, and cerium.

8. A process according to claim 1, wherein the catalyst has a composition represented by the empirical formula

$$Me_aSb_bX_cQ_dR_eO_f(SiO_2)_g$$

wherein
- Me represents at least one element selected from the group consisting of Fe, Co, Ni, Sn, U, Cr, Cu, Mn, Ti, Th, and Ce;
- X represents at least one element selected from the group consisting of V, Mo, and W;
- Q represents at least one element selected from the group consisting of Li, Na, K, Rb, Cs, Be, Mg, Ca, Sr, Ba, Y, La, Th, Zr, Hf, Nb, Ta, Re, Ru, Os, Rh, Ir, Pd, Pt, Ag, Zn, Cd, Al, Ga, In, Tl, Ge, Pb, As, and Se;
- R represents at least one element selected from the group consisting of B, P, Te, and Bi; and the subscripts a, b, c, d, e, and g represents atomic ratios and are respectively within the ranges
  - a is from 5 to 15;
  - b is from 5 to 100;
  - c is from 0 to 15;
  - d is from 0 to 20;
  - e is from 0 to 10;
  - g is from 10 to 200; and
- f refers to the number of oxygen atoms present in an oxide as formed by bonding the respective constituent elements.

* * * * *